United States Patent
Ye et al.

(10) Patent No.: US 12,245,804 B2
(45) Date of Patent: Mar. 11, 2025

(54) PORTABLE MINIMALLY INVASIVE SURGICAL MECHANICAL ARM WITH MULTI-DEGREE OF FREEDOM

(71) Applicant: SHANGHAI SINZEN MEDTECH LTD., Shanghai (CN)

(72) Inventors: Chunhua Ye, Shanghai (CN); Chunying Zhao, Shanghai (CN)

(73) Assignee: SHANGHAI SINZEN MEDTECH LTD., Shanghai (CN)

( * ) Notice: Subject to any disclaimer, the term of this patent is extended or adjusted under 35 U.S.C. 154(b) by 0 days.

(21) Appl. No.: 18/686,270

(22) PCT Filed: May 18, 2022

(86) PCT No.: PCT/CN2022/093662
§ 371 (c)(1),
(2) Date: Feb. 23, 2024

(87) PCT Pub. No.: WO2023/024600
PCT Pub. Date: Mar. 2, 2023

(65) Prior Publication Data
US 2025/0000572 A1    Jan. 2, 2025

(30) Foreign Application Priority Data
Aug. 23, 2021  (CN) .......................... 202110968127.2

(51) Int. Cl.
*A61B 17/29*  (2006.01)
*A61B 18/14*  (2006.01)
(Continued)

(52) U.S. Cl.
CPC .......... *A61B 18/1482* (2013.01); *A61B 34/30* (2016.02); *A61B 34/71* (2016.02);
(Continued)

(58) Field of Classification Search
CPC ................... A61B 34/30; A61B 34/71; A61B 2017/00389; A61B 2017/00424;
(Continued)

(56) References Cited

U.S. PATENT DOCUMENTS 7,090,689 B2 *  8/2006  Nagase .................. A61B 17/29
                                                    606/174
7,549,998 B2 *  6/2009  Braun ................ A61B 17/2909
                                                    606/205
(Continued)

FOREIGN PATENT DOCUMENTS

CN    102921089 A    2/2013
CN    103877663 A    6/2014
(Continued)

OTHER PUBLICATIONS

Request for the Submission of an Opinion issued for Korean Patent Application No. 10-2024-7009446, dated Apr. 22, 2024, 11 pages including English machine translation.
(Continued)

*Primary Examiner* — Michael F Peffley
(74) *Attorney, Agent, or Firm* — HSML P.C.

(57) ABSTRACT

A portable minimally invasive surgical mechanical arm with multi-degree of freedom comprises a handle joint assembly which is used for movably mounting an axle part, and the assembly comprises a first axis and second axis allowing the axle part to rotate around the first axis and the second axis respectively. The first axis coincides with the axis of the axle part, and the second axis is perpendicular to a shaft. A controlling mechanism and a controlling wire joint assembly are used for transmitting the motion of the grip part to the controlling wire joint assembly. The controlling mechanism comprises an input piece, two push rods and an output piece, and the two push rods. The input piece receives the output
(Continued)

motion of the axle part, and the output piece is part of the controlling wire joint.

12 Claims, 14 Drawing Sheets

(51) Int. Cl.
*A61B 34/00* (2016.01)
*A61B 34/30* (2016.01)
*A61B 17/00* (2006.01)
*A61B 18/00* (2006.01)

(52) U.S. Cl.
CPC ............... *A61B 2017/00389* (2013.01); *A61B 2017/00424* (2013.01); *A61B 2018/00958* (2013.01); *A61B 2034/301* (2016.02)

(58) Field of Classification Search
CPC .... A61B 2017/2901; A61B 2017/2841; A61B 2017/2908; A61B 2017/2909; A61B 2017/291; A61B 2017/2919; A61B 2017/2912; A61B 2017/2918; A61B 2017/2926; A61B 2034/301
USPC .......................................................... 606/45
See application file for complete search history.

(56) References Cited

U.S. PATENT DOCUMENTS

| 2011/0144576 | A1 | 6/2011 | Rothe et al. |
| 2013/0012929 | A1 | 1/2013 | Malkowski |
| 2013/0178712 | A1 | 7/2013 | Malkowski et al. |
| 2018/0125519 | A1* | 5/2018 | Beira ................. A61B 17/2909 |
| 2021/0045825 | A1* | 2/2021 | Lee ........................ A61B 34/71 |

FOREIGN PATENT DOCUMENTS

| CN | 103953859 A | 7/2014 |
| CN | 105437205 A | 3/2016 |
| CN | 108605557 A | 10/2018 |
| CN | 110575604 A | 12/2019 |
| CN | 111110985 A | 5/2020 |
| CN | 112128224 A | 12/2020 |
| CN | 112244949 A | 1/2021 |
| CN | 213552663 U | 6/2021 |
| CN | 113171180 A | 7/2021 |
| CN | 113476144 A | 10/2021 |

OTHER PUBLICATIONS

International Search Report issued for International Patent Application No. PCT/CN2022/093662, Date of mailing: Aug. 16, 2022, 8 pages including English translation.

* cited by examiner ized surgical system represented by da Vinci surgical robot has high precision, high efficiency and powerful function, and both doctors and patients have good practical experience. However, due to the complex and bulky structure, expensive cost, complex procedure of operation and maintenance, the application range is limited. And additionally, the price of da Vinci surgical robot service is not acceptable for patients with limited economic conditions.

PORTABLE MINIMALLY INVASIVE SURGICAL MECHANICAL ARM WITH MULTI-DEGREE OF FREEDOM

This application is a national stage filing under 35 U.S.C. § 371 of international application number PCT/CN2022/093662, filed May 18, 2022, which claims priority to Chinese patent application No. 202110968127.2, filed Aug. 23, 2021. The contents of these applications are incorporated herein by reference in their entirety.

TECHNICAL FIELD

The disclosure is related to medical device, especially a portable minimally invasive surgical mechanical arm with multi-degree of freedom.

BACKGROUND

Along with the progress in medical science, minimally invasive surgery gains popularity in clinic treatment with advantages of smaller wounds, less pain and faster recovery. Specific mechanical arms are essential to performing the operation in a laparoscopic or thoracoscopic surgery.

In endoscopic surgeries, surgical instruments can only penetrate into the patient's body through a small incision of about 1 cm on the patient's body to perform complex surgical actions such as exploration, cutting, hemostasis and suturing, which put forward high requirements for mechanical arms with high degree of freedom. At present, the sophisticated minimally invasive surgical system represented by da Vinci surgical robot has high precision, high efficiency and powerful function, and both doctors and patients have good practical experience. However, due to the complex and bulky structure, expensive cost, complex procedure of operation and maintenance, the application range is limited. And additionally, the price of da Vinci surgical robot service is not acceptable for patients with limited economic conditions.

Therefore, various minimally invasive surgical mechanical arms have become the most convenient choice in the current minimally invasive surgery. The basic structure of the minimally invasive surgical mechanical arm comprises a blade part, a blade joint assembly, a shaft and a handle. The blade part and the handle are respectively installed at the two ends of the shaft, controlling wires are disposed inside the shaft, and a joint assembly for controlling wire is disposed at the end near the handle so that the blade joint assembly at the other end can be controlled by the handle. Degrees of freedom of the prior mechanical arms are limited, the flexibility of the blade joint assembly is not satisfying which makes the operation inefficient. And as the handle is coaxial with the shaft, the operation posture is inconsistent with the requirements of ergonomics which causes fatigue to the user. Such limitation has negative effects on the efficiency and safety of the operation.

SUMMARY

The objective of the disclosure is to provide a portable minimally invasive surgical mechanical arm with multi-degree of freedom, the blade part of which can swing and rotate freely, simplifying the operation and improving the ergonomics.

A portable minimally invasive surgical mechanical arm with multi-degree of freedom comprises a blade part, a blade joint assembly, a shaft and a handle. The blade part is installed at one end of the shaft by the blade joint assembly, and the handle is installed at the other end of the shaft. The shaft comprises a plurality of controlling wires and a controlling wire joint assembly arranged at the other end. The controlling wire joint assembly and the blade joint assembly are connected by the plurality of controlling wires. The handle comprises a grip part, a handle joint assembly and a controlling mechanism. The grip part comprises a grip portion and an axle part. The axle part is movably connected to the handle joint assembly and the handle joint assembly comprises a first axis and a second axis that are mutually perpendicular to each other allowing the axle part to rotate around the first axis and the second axis respectively, wherein the first axis coincides with the axis of the axle part, and the second axis is perpendicular to the shaft. The controlling mechanism connects the axle part and the controlling wire joint assembly, and is used for transferring the movement of the handle to the controlling wire joint assembly. The controlling mechanism comprises a four-link mechanism, and the four-link mechanism comprises an input piece, two push rods and an output piece, and the two push rods are connected with the input piece and the output piece respectively, with the input piece receiving movements of the axle part and the output piece being a part of the controlling wire joint assembly.

Preferably, the grip part is set on one side of the shaft, so that a holding direction of the grip part is intersected with an axial direction of the shaft.

The user can grasp and operate the mechanical arm with a more natural gesture, so that it is flexible and convenient to operate the mechanical arm and the ergonomics can be improved. The user can control the blade joint assembly by moving the wrist of the holding hand, dispense with double-hand operating and simplifying the operation method.

Preferably, the grip part also comprises a shell fixedly installed with respect to the shaft, and the shell accommodates the handle joint assembly and the controlling mechanism. The handle joint assembly comprises an inner cylinder with the first axis as an axis, the inner cylinder is nested in the shell, and the inner cylinder can rotate around its own axis relative to the shell. The axle part is connected to the inner cylinder with a pivot and is axially aligned with the inner cylinder; and the pivot is arranged along the second axis.

Preferably, the grip part also comprises a shell fixed to the shaft, and the shell accommodates the handle joint assembly and the controlling mechanism. The handle joint assembly comprises an inner cylinder and an outer cylinder with the first axis as an axis, and the axle part is set in the inner cylinder being rotatable around its own axis relative to the outer cylinder, and the outer cylinder is connected to the shell with a pivot, and the pivot is arranged along the second axis.

Preferably, the handle also comprises a shell fixed to the shaft and the shell accommodates the handle joint assembly and the controlling mechanism. The handle joint assembly is a ball joint including a joint ball and a support socket, and the joint ball is set at the end nearer to the shaft of the axle part, while the support socket is fixed on the shell, and an axis of an opening of the support socket is the first axis.

Preferably, the controlling wire joint assembly comprises a third axis and a fourth axis perpendicular to each other, allowing the controlling wire joint assembly to rotate in the same direction with the axle part to drive the controlling wires, so that the blade joint assembly is driven to bend. Because of the controlling wire joint assembly, the blade joint assembly bend in the direction same with the user's wrist gesture which is customary to the operation habit in the operation.

Preferably, the input piece of the four-link mechanism is a push-rod-plate, and the center of the push-rod-plate is on the first axis, and the push-rod-plate is pivotedly connected with the axle part in the direction parallel to the second axis. In operation, the push-rod-plate can rotate around the first axis, which makes the controlling mechanism small and compact. The bending moment of the push rods is reduced due to the pivoted connection with the axle part improving the service life of the part.

Preferably, the handle comprises a locking system, and the locking system comprises a locking switch, a locking transmission and a brake. The locking switch is located on the grip part, and the locking switch is connected to one end of the locking transmission while the brake is connected to the other end of the locking transmission. The locking switch has two states of locking and releasing, and when the locking switch is in the state of locking, the locking transmission drives the brake to a locking position to lock the handle joint assembly or the input piece of the four-link mechanism, so that the four-link mechanism is frozen; and when the locking switch is in the state of releasing, the brake moves out of the locking position leaving the input piece movable. The blade joint assembly can be locked by the locking system in operation so that the blade part is in a fixed position improving the operation safety.

Preferably, the handle comprises a blade switch rod and a blade controlling wire, and the blade switch rod is connected with the blade part through the blade controlling wire to make the blade part open or close. The blade switch rod is installed on the grip part. The blade switch rod and the grip part are arranged in the shape of herringbone, so that a user can pull the blade switch rod with fingers when holding the grip portion in hand. The handle also comprises a blade rotating knob, and the blade rotating knob is connected with the blade part through an elastic shaft for controlling the blade part rotating around its axis. The blade rotating knob is installed on the grip part and is set in an upper location to the blade switch rod allowing a user to turn the blade rotating knob with an index finger when holding the grip portion. The user can hold the handle and make the mechanical arm perform bending, rotating, locking and making the blade part open or close with one hand, avoiding double-hand operating, simplifying the operation, and improving the efficiency of surgeries.

Optionally, the blade part comprises electrosurgical instruments, and both of the shaft and the handle contain power lines for the electrosurgical instruments. The handle comprises an electrosurgical instrument switch, which is adjacent to the blade rotating knob allowing a user to operate the electrosurgical instrument switch with an index finger when holding the grip portion.

Preferably, the axle part is hollow allowing the blade controlling wire and the elastic shaft extend through the axle part. The hollow axle part compacts the handle, optimizes the volume and reduces the weight.

Optionally, the shaft comprises a straight segment and a bending segment, and the straight segment and the handle are connected by the bending segment with the grip part of the handle located on an extension cord of the straight segment. The bending segment allows the relative position of the handle and the knife head to be adjusted according to the actual use scenario, making the operation more flexible.

INDEX OF THE DRAWING REFERENCE SIGNS

1—blade part;
2—blade joint assembly;
3—shaft;
4—handle;
5—grip part;
6—shell;
7—controlling mechanism;
8—axle part;
9—fulcrum rod;
10—push-rod-plate;
11—push rod;
12—controlling wire joint assembly;
13—controlling wire;
14—first axis;
15—outer cylinder;
16—inner cylinder;
17—pivot with a second axis;
18—third axis;
19—fourth axis;
20—locking switch;
21—locking transmission;
22—brake;
23—elastic restorer;
24—blade switch rod;
25—blade rotating knob;
26—powe line;
27—electrosurgical instrument switch;
28—stopper;
29—blade controlling wire;

30—elastic shaft;
31—joint ball;
32—brake window;
33—support socket;
34—brake pad;
35—brake pivot;
36—bending segment.

Previous figures are presented for a fuller understanding of the nature and design objects rather than as restriction for embodiments of the present invention. Wherein the x, y, z are coordinate system set for better illustrating the spatial relationship in the figures. The meanings of the signs and coordinate systems in each Fig. remain consistent. The previous figures are schematic illustration of the embodiments rather than accurate drawings including all the details of the parts.

DETAILED DESCRIPTION

Further detailed description shall be made by the following embodiments in conjunction with the drawings.

Figure 1:
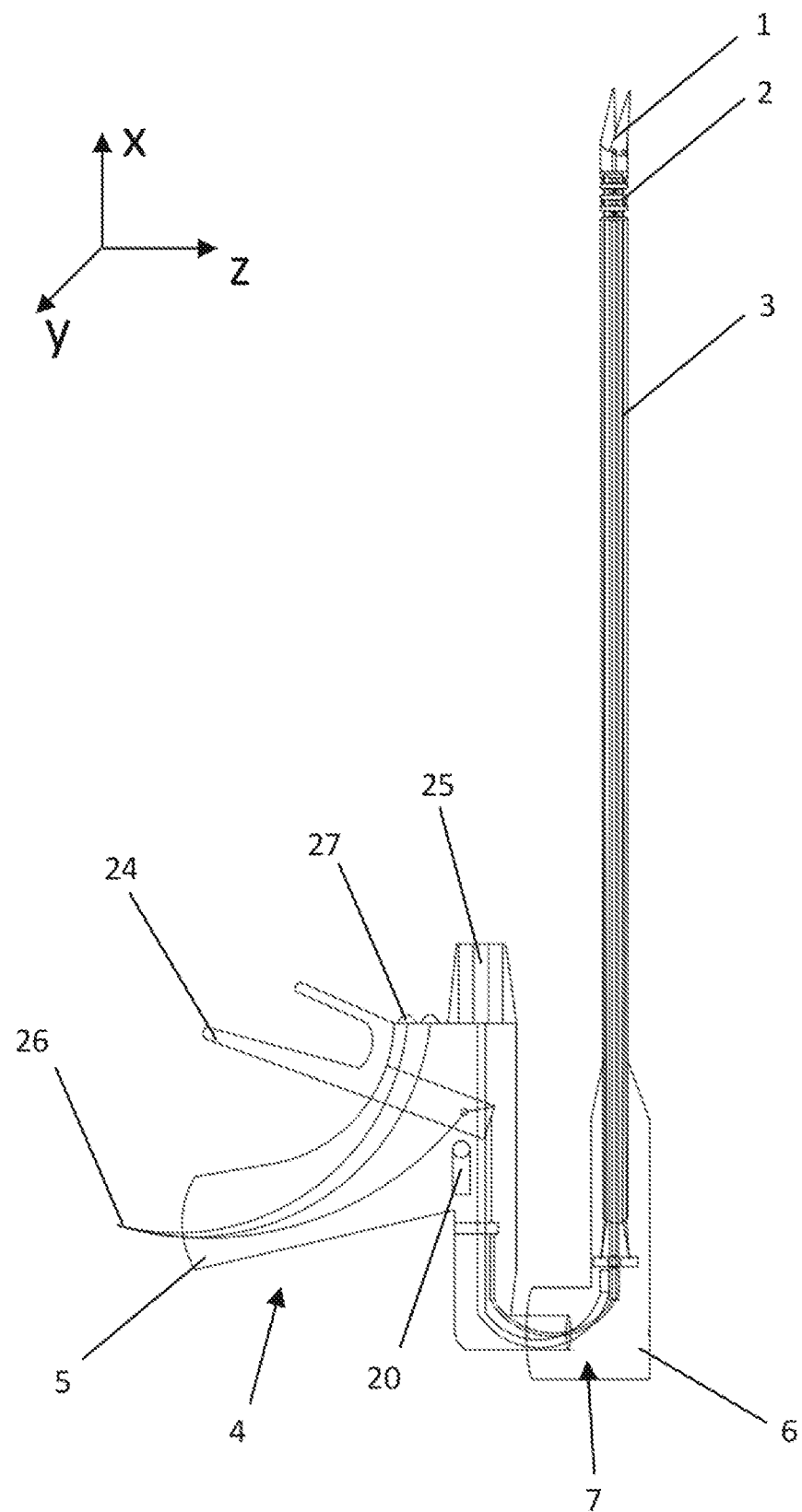
FIG. 1 is a schematic view showing the structure of a portable minimally invasive surgical mechanical arm with multi-degree of freedom.

FIG. 1 is a schematic view showing the structure of a portable minimally invasive surgical mechanical arm with multi-degrees of freedom. The blade part 1 is connected to one end of the shaft 3 through the blade joint assembly 2, and the other end of the shaft 3 is connected to the handle 4. The handle 4 comprises a shell 6, a controlling mechanism 7 and a grip part 5. The shell 6 is fixed with the shaft 3, and the controlling mechanism 7 is installed inside the shell 6. According to FIG. 2, one end of the grip part 5 is the axle part 8, and the axle part 8 is inserted into the shell 6. The user holds the other end of the grip part 5, namely a grip portion, to operate the mechanical arm. When the user holds the grip part 5, the thumb is positively oriented towards the z-axis relative to the palm, and this direction is defined as the holding direction.

Figure 2:
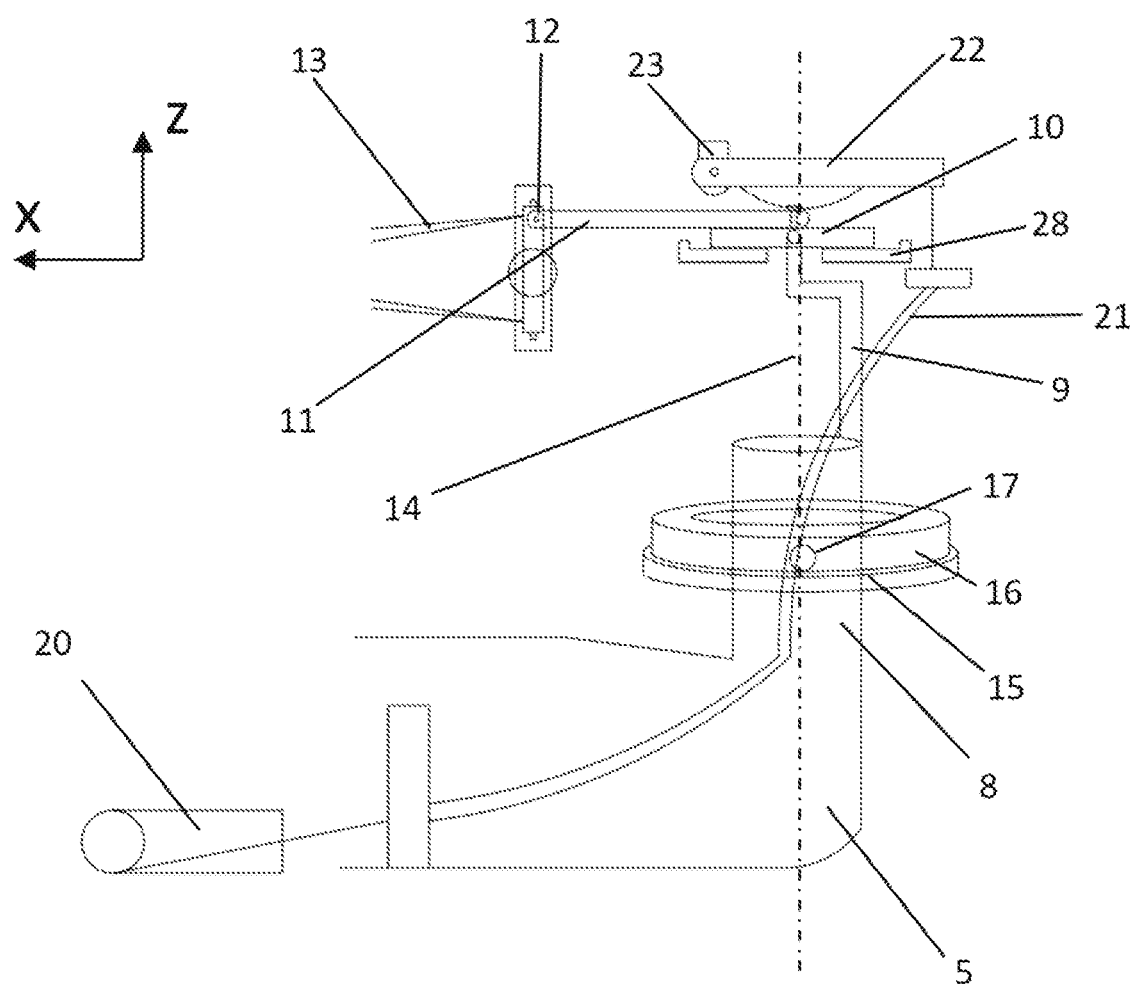
FIG. 2 is a schematic view showing the structure of a controlling mechanism and a handle joint assembly.
Figure 3:
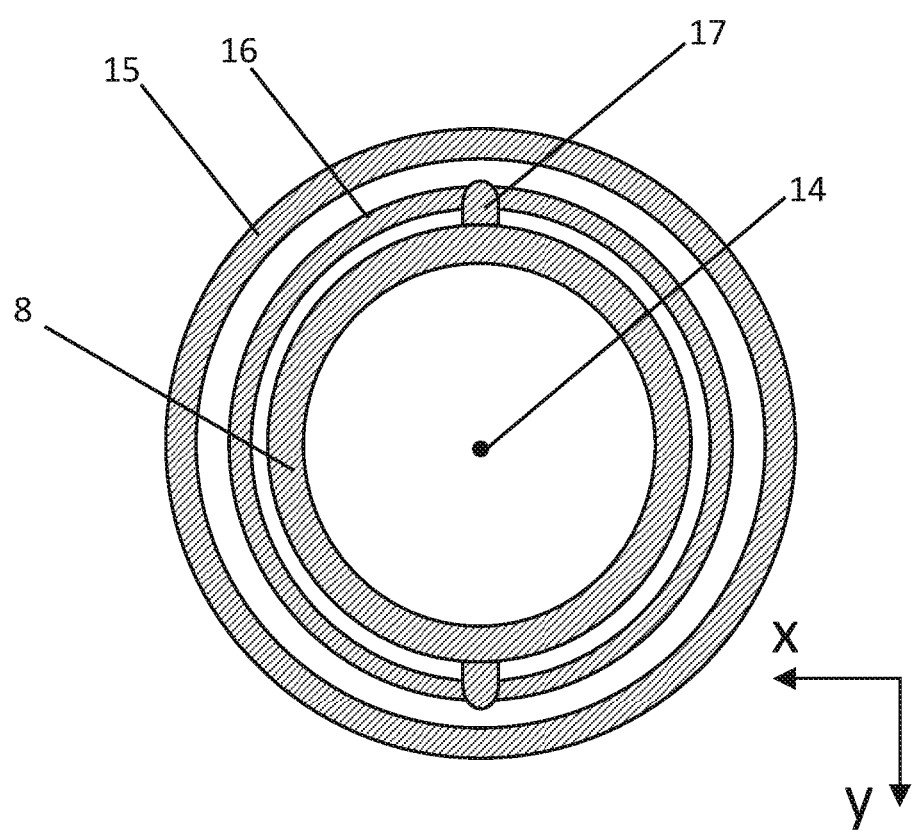
FIG. 3 is a sectional view of a handle joint assembly.

As shown in FIGS. 2 and 3, a handle joint assembly is installed inside the shell 6, wherein the handle joint assembly comprises an outer cylinder 15, an inner cylinder 16 and a pivot 17 with a second axis. The inner cylinder 16 can rotate around the first axis 14 in the z-axis direction relative to the outer cylinder 15, and the axial direction of the pivot 17 with the second axis is the second axis. The axle part 8 is connected with the inner cylinder 16 through the second rotating axis pivot 17, and the axle part 8 can rotate around the second axis through the pivot 17 with the second axis. A fulcrum rod 9 is fixed on the axle part 8, and it is connected with the controlling mechanism 7. The controlling mechanism 7 comprises a push-rod-plate 10 and two push rods 11, the push-rod-plate 10 is pivotedly connected with the fulcrum rod 9, allowing the push-rod-plate 10 to rotate around the y-axis relative to the fulcrum rod 9, and the position of the connection point is on the first axis 14. According to FIG. 9, the two push rods 11 are pivotedly connected with the controlling wire joint assembly 12, and the push-rod-plate 10, the push rods 11 and the controlling wire joint assembly 12 form a four-link mechanism with the push-rod-plate 10 being an input piece receiving the movement input by the fulcrum rod 9 and driving the controlling wire joint assembly 12. The fulcrum rod 9 and the push rods 11 are rods with some flexibility.

Figure 4:
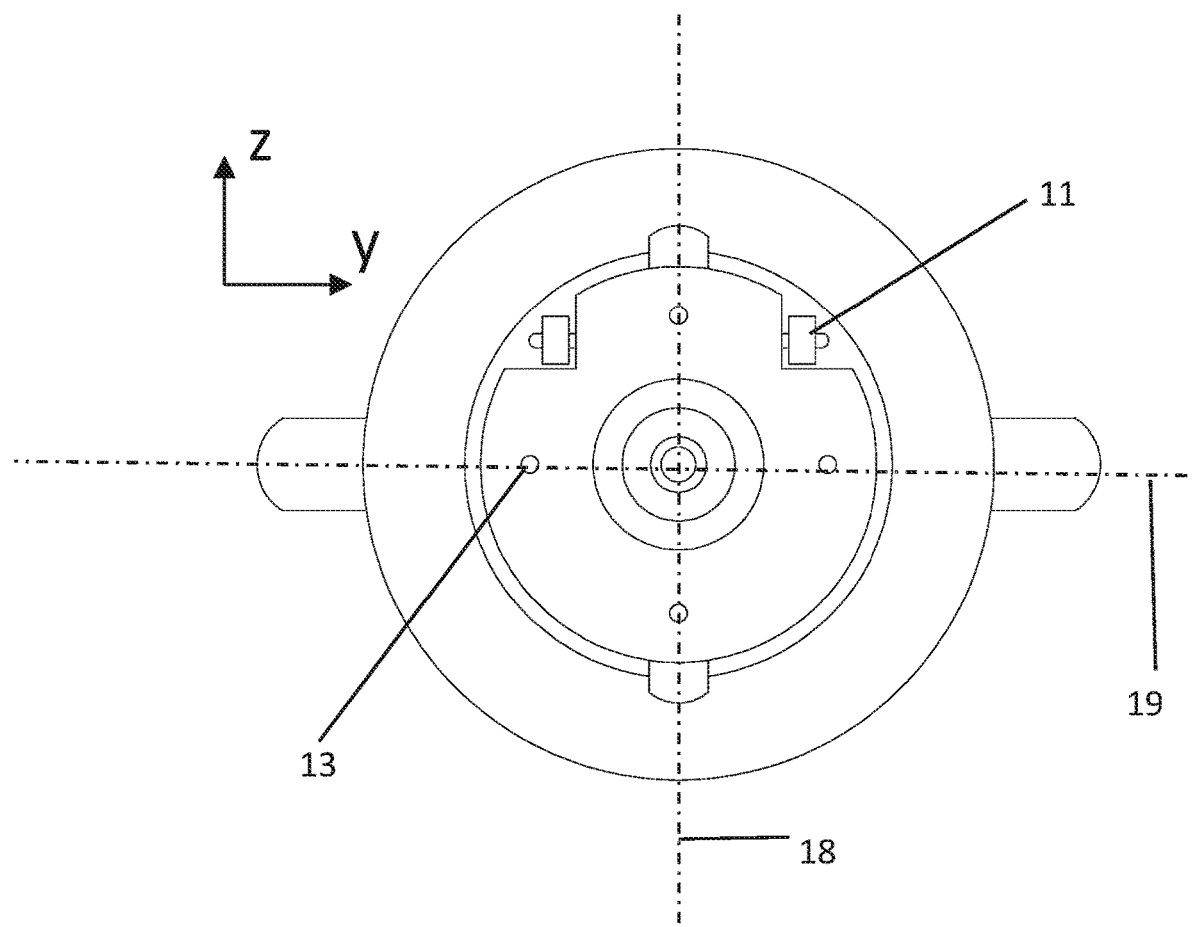
FIG. 4 is a schematic view showing the structure of a controlling wire joint assembly.

The structure of the controlling wire joint assembly 12 is shown in FIG. 4, it comprises two pivots, and one of the pivots is arranged on the third axis 18 and the other of the pivot is arranged on the fourth axis 19 of the controlling wire joint, so that the controlling wire joint assembly 12 can rotate around the third axis 18 and the fourth axis 19 respectively. According to FIG. 9, the two push rods 11 are pivotedly connected to the controlling wire joint assembly and installation position is above the fourth axis 19. One end of multiple controlling wires 13 is fixed on the controlling wire joint assembly 12, and the other end is fixed on the blade joint assembly 2 (including the case that the controlling wires directly fixed on the blade part 1).

When the mechanical arm is utilized in operation, the shaft 3 is inserted into the patient's body through a surgical incision, and its position is relatively fixed. The user holds the grip part 5 with one hand, makes the axle part 8 rotate by moving the wrist of the holding hand, so that the bending blade joint assembly drives the blade part towards a direction required by surgical operation.

Figure 5:
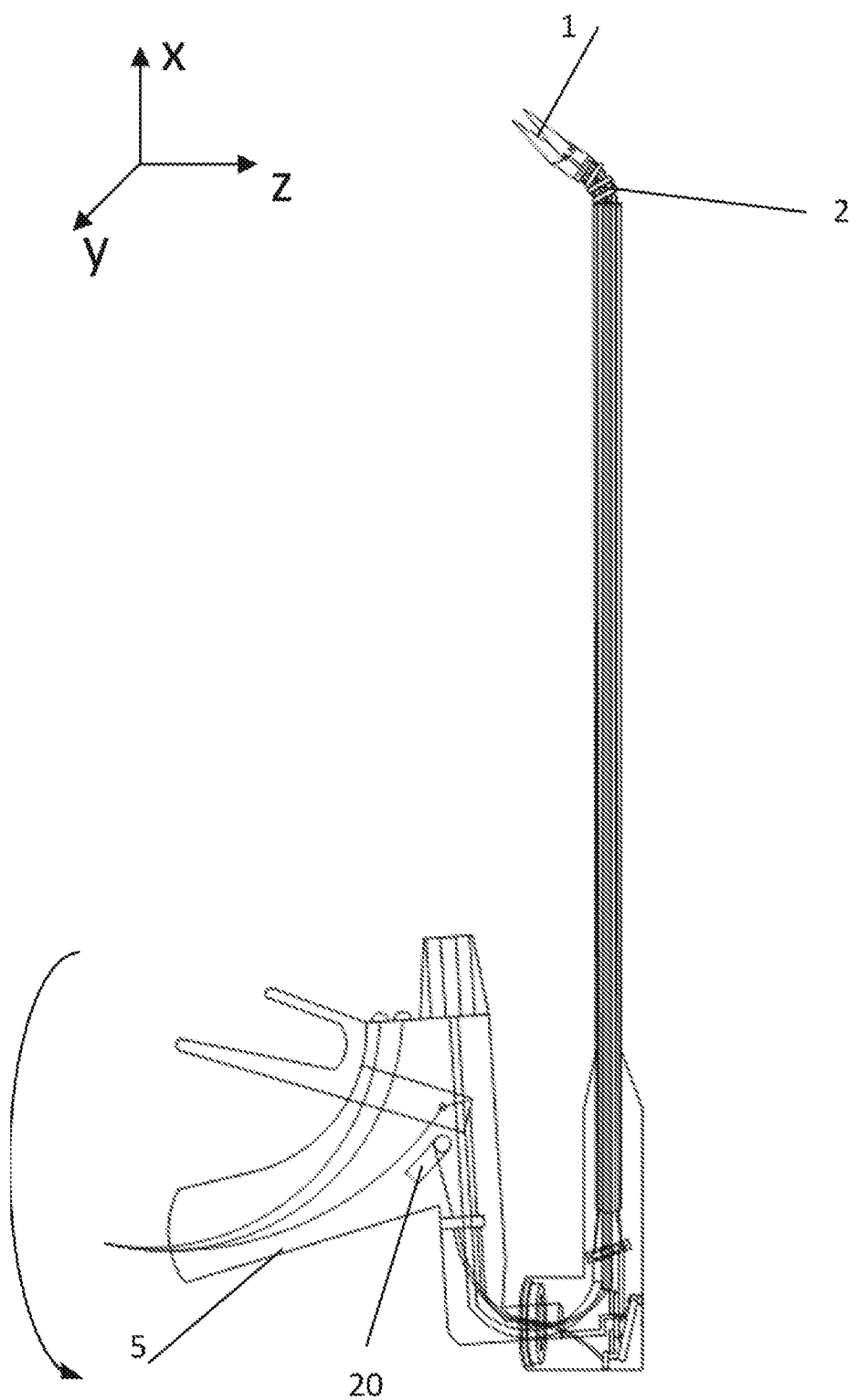
FIG. 5 is a schematic view showing a blade joint assembly of a portable minimally invasive surgical mechanical arm bending in xz plane.

FIG. 5 is a schematic view of the blade part 1 swinging in the xz-plane. When the blade part 1 is required to swing towards the negative direction of the z-axis, the grip part 5 is made to rotate counterclockwise around the second axis 17 according to the direction of the arrow, so that the blade joint assembly 2 is driven to bend to the negative direction of the z axis by the controlling mechanism 7. The movement of the controlling mechanism 7 can be demonstrated in combination with FIG. 6, where the grip part 5 rotates counterclockwise around the pivot 17 with the second axis along the direction of the arrow, driving the fulcrum rod 9 and the push-rod-plate 10 to move together, and the push-rod-plate 10 drives the push rods 11 to move forward in the positive direction of the x-axis, and pushes the controlling wire joint assembly 12 to rotate counterclockwise around the fourth axis 19 of the controlling wire joint assembly. At this time, the upper controlling wire 13 is relaxed, and the lower controlling wire 13 is tightened, thus driving the blade joint assembly 2 to bend towards the negative direction of the z-axis. The stopper 28 plays a restricting role in the movement range of the push-rod-plate 10, to avoid its movement exceeding the acceptable range of the controlling wire joint assembly 12.

As the fulcrum rod 9 and the push rods 11 are flexible rods, the motion component, which generated by the push-rod-plate 10 following the fulcrum rod 9 rotating around the pivot 17 with the second axis in the z-axis direction, can be absorbed by the elastic deformation of the fulcrum rod 9 and the push rods 11, reducing the stress of the hinge structure; the push-rod-plate 10 is pivotedly connected with the fulcrum rod 9, and can rotate around the y-axis, eliminating the angle change caused by the rotation of the fulcrum rod 9, so that the push-rod-plate 10 is always parallel to the xy-plane, optimizing the stress state of the fulcrum rod 9 and the push-rod-plate 10. As a result, the service life of the relevant parts are prolonged and the reliability of the mechanical arm is improved.

Figure 7:
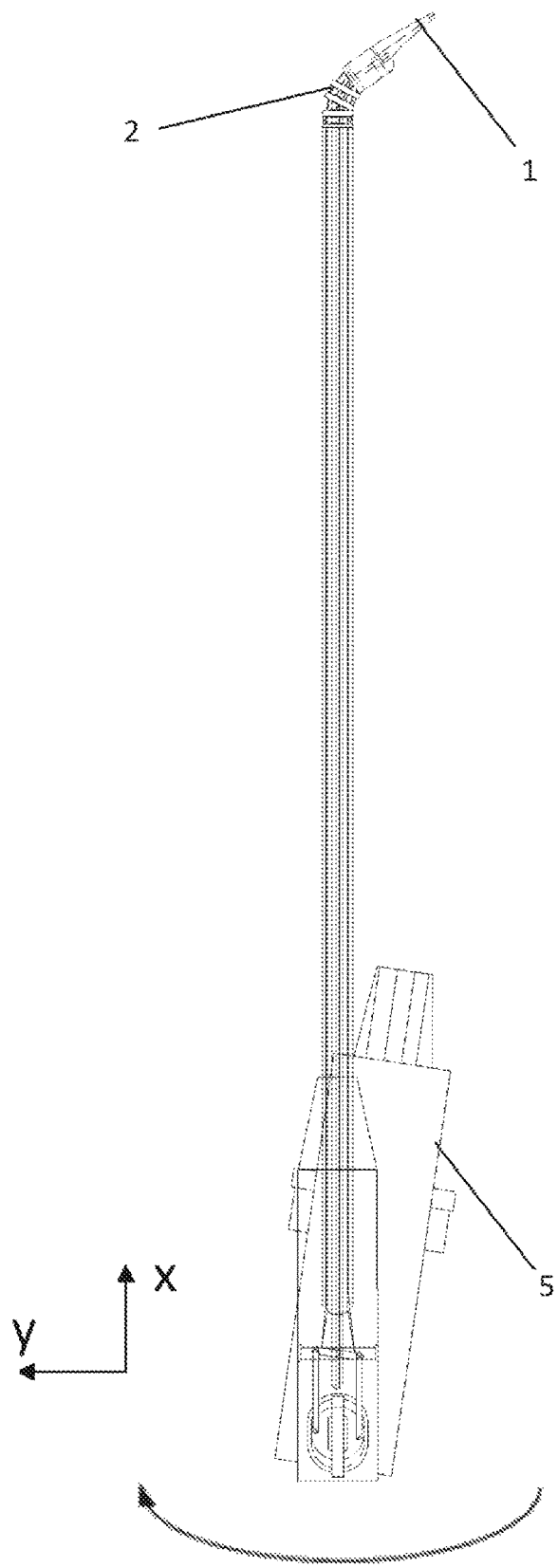
FIG. 7 is a schematic view showing a blade joint assembly of a portable minimally invasive surgical mechanical arm bending in xy plane.
Figure 8:
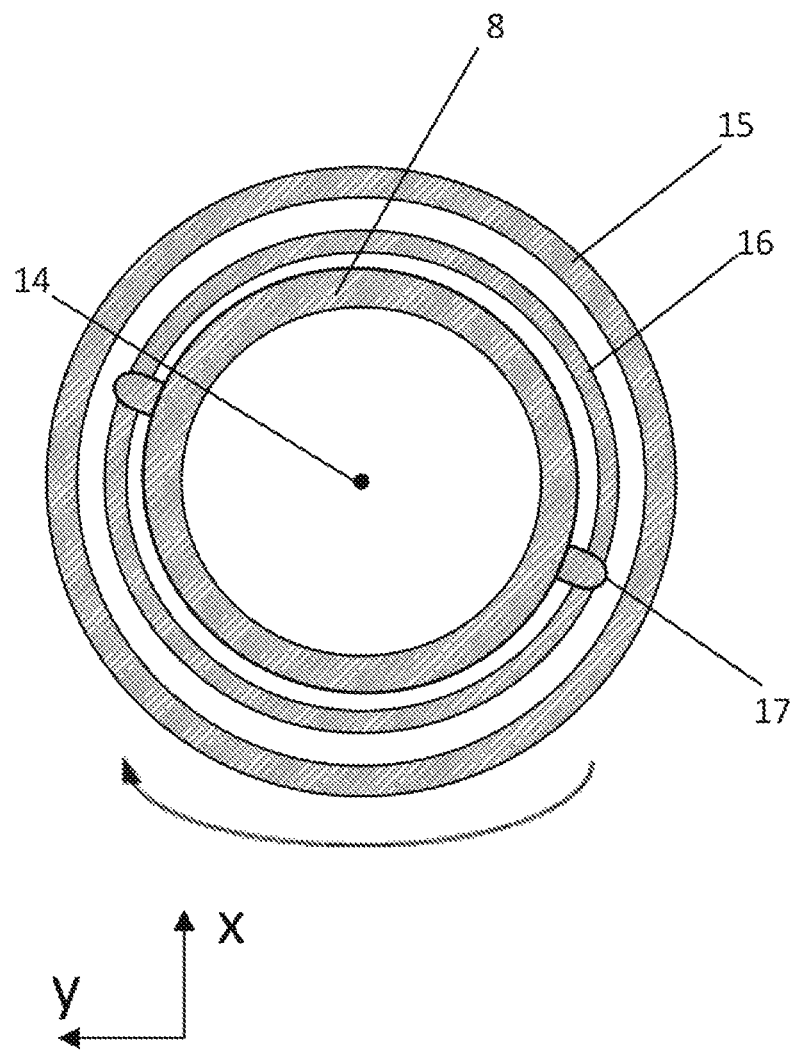
FIG. 8 is a schematic view showing the status of a handle joint assembly when a blade joint assembly bending in xy plane.
Figure 9:
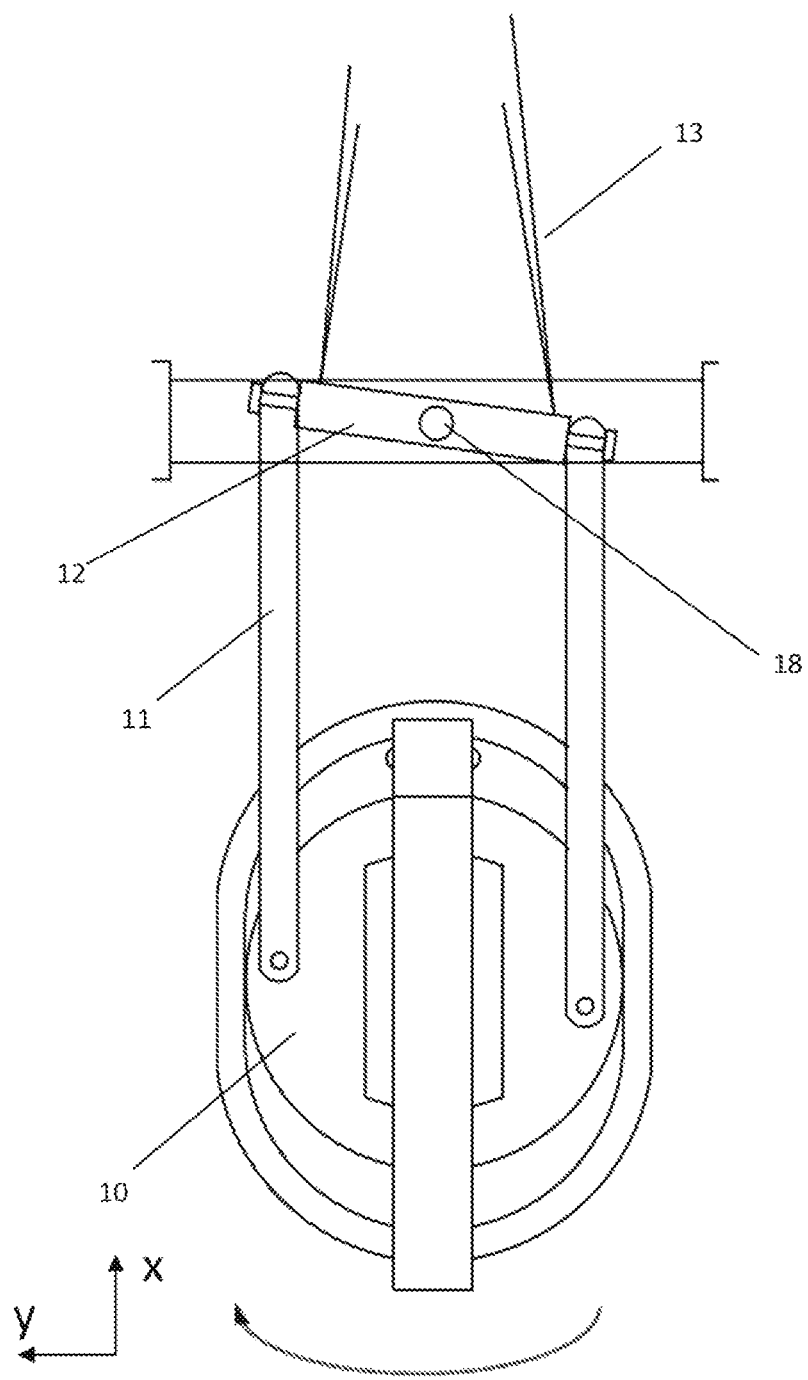
FIG. 9 is a schematic view showing the status of a controlling mechanism when a blade joint assembly bending in xy plane.

FIG. 7 is a schematic view of blade part 1 swinging towards the negative direction of y-axis. When the blade part 1 is required to swing towards the negative direction of the y-axis as shown in FIG. 7, as FIG. 8 illustrates that the axle part 8 rotates clockwise around the first axis 14 according to the direction of the arrow, and the controlling wire joint assembly 12 is driven to the right by the controlling mechanism 7. As shown in FIG. 9, the push-rod-plate 10 is driven by the axle part 8 to rotate clockwise around the first axis 14, so that the controlling wire joint assembly 12 is driven to rotate clockwise around the third axis 18 of the controlling wire joint assembly by the two push rods 11. During this process, the controlling wires 13 on the left are relaxed and the controlling wires 13 on the right are tightened, so that the blade joint assembly 2 is bent towards the negative direction of the y axis.

Figure 6:
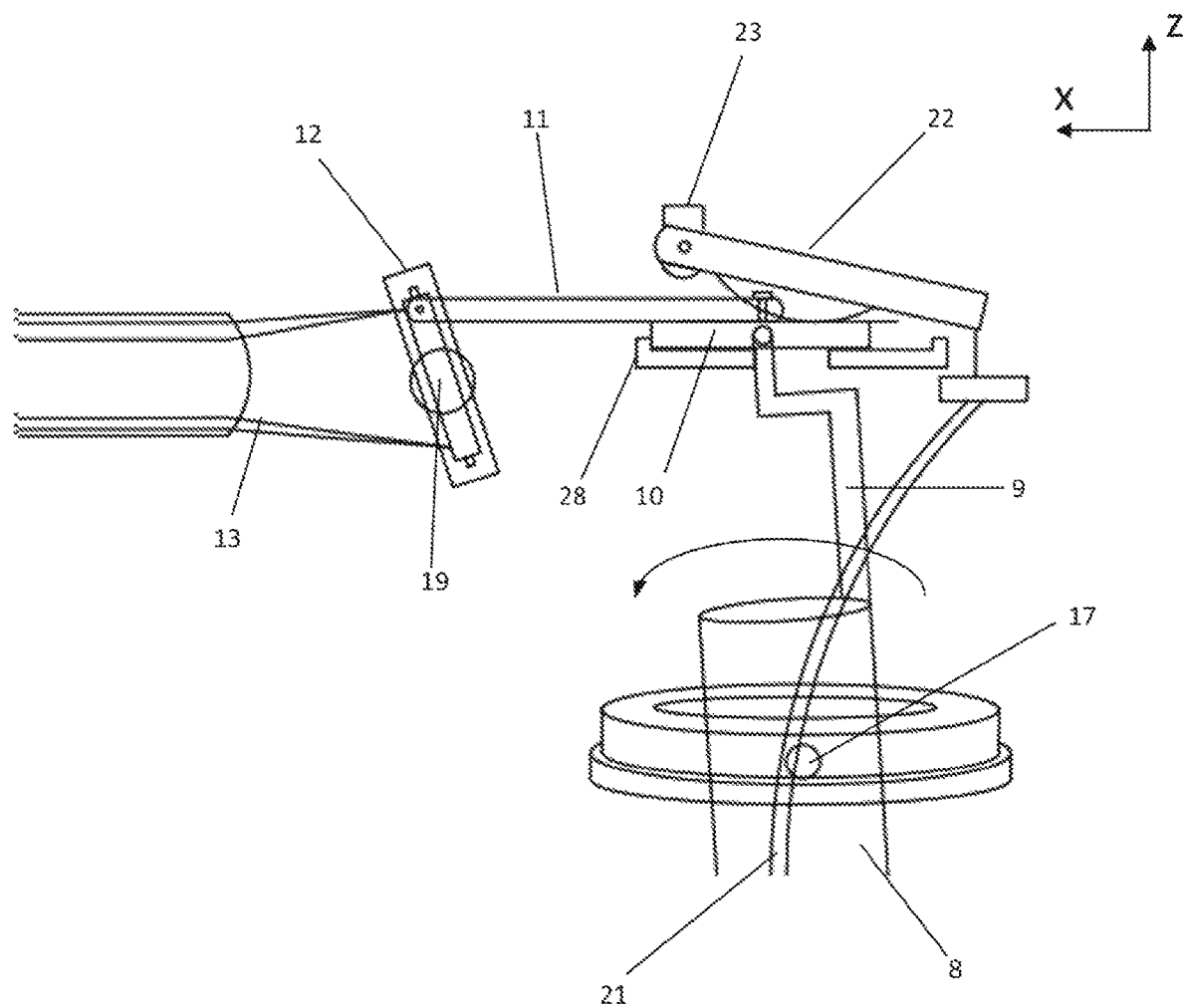
FIG. 6 is a schematic view showing the status of a controlling mechanism and a handle joint assembly when a blade joint assembly bending in xz plane.

As shown in FIG. 1 and FIG. 2, the handle 4 comprises a locking system including a locking switch 20, a locking transmission 21, a brake 22 and an elastic restorer 23. The locking transmission 21 is a locking controlling wire, one end of which is connected with the locking switch 20 and the other end is connected with the brake 22, and the brake is connected to the shell 6 through the elastic restorer 23. As shown in FIG. 6, when the blade joint assembly is bent to the predetermined position, the locking switch 20 is turned to the locking position, and the locking transmission 21 is driven to bring the brake 22 to press the push-rod-plate 10, so that the push-rod-plate 10 is prevented from moving, locking the blade joint assembly. When the locking switch 20 is turned to the releasing position, the locking transmission 21 is relaxed, and the brake 22 moves away from the push-rod-plate 10 under the drive of the elastic restorer 23, and the blade joint assembly is unlocked. The brake 22 is a friction plate, and the elastic restorer 23 is a reed or spring shaft. When the locking switch 20 is in the locking position, the brake 22 swings in the negative direction of the z-axis and presses the push-rod-plate 10 together with the stopper 28, so that the push-rod-plate 10 is locked by the friction. When the locking switch 20 is in the releasing position, the brake 22 swings in the positive direction of the z-axis and moves away from the push-rod-plate 10 under the elastic force of the elastic restorer 23, so as to restore the freedom of movement of the push-rod-plate.

Figure 12:
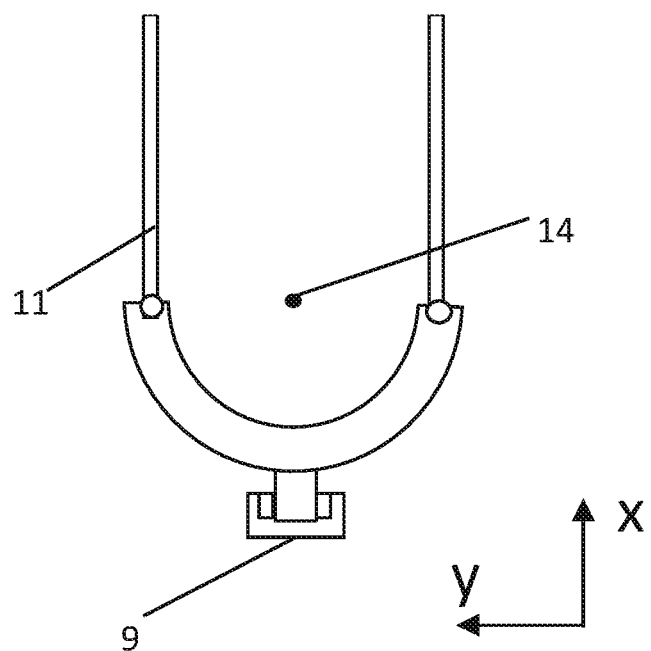
FIG. 12 is a schematic view showing the structure of a controlling system.

In another embodiment, as shown in FIG. 12, the push-rod-plate 10 is replaced by a "Y" shaped fork arm. One end of the fork arm is pivotedly connected with the fulcrum rod 9, so that the fork arm can rotate around the y-axis direction relative to the fulcrum rod 9. The other end is pivotedly connected with two push rods 11, and the fork arm can rotate around the first axis 14 driven by the fulcrum rod 9. The brake 22 is configured as a brake caliper. When the locking switch 20 is in the locking position, the fork arm is clamped by the brake caliper and is immovable. When the locking switch 20 is in the releasing position, the brake caliper frees the fork arm, so as to restore the movability of the folk arm.

Figure 10:
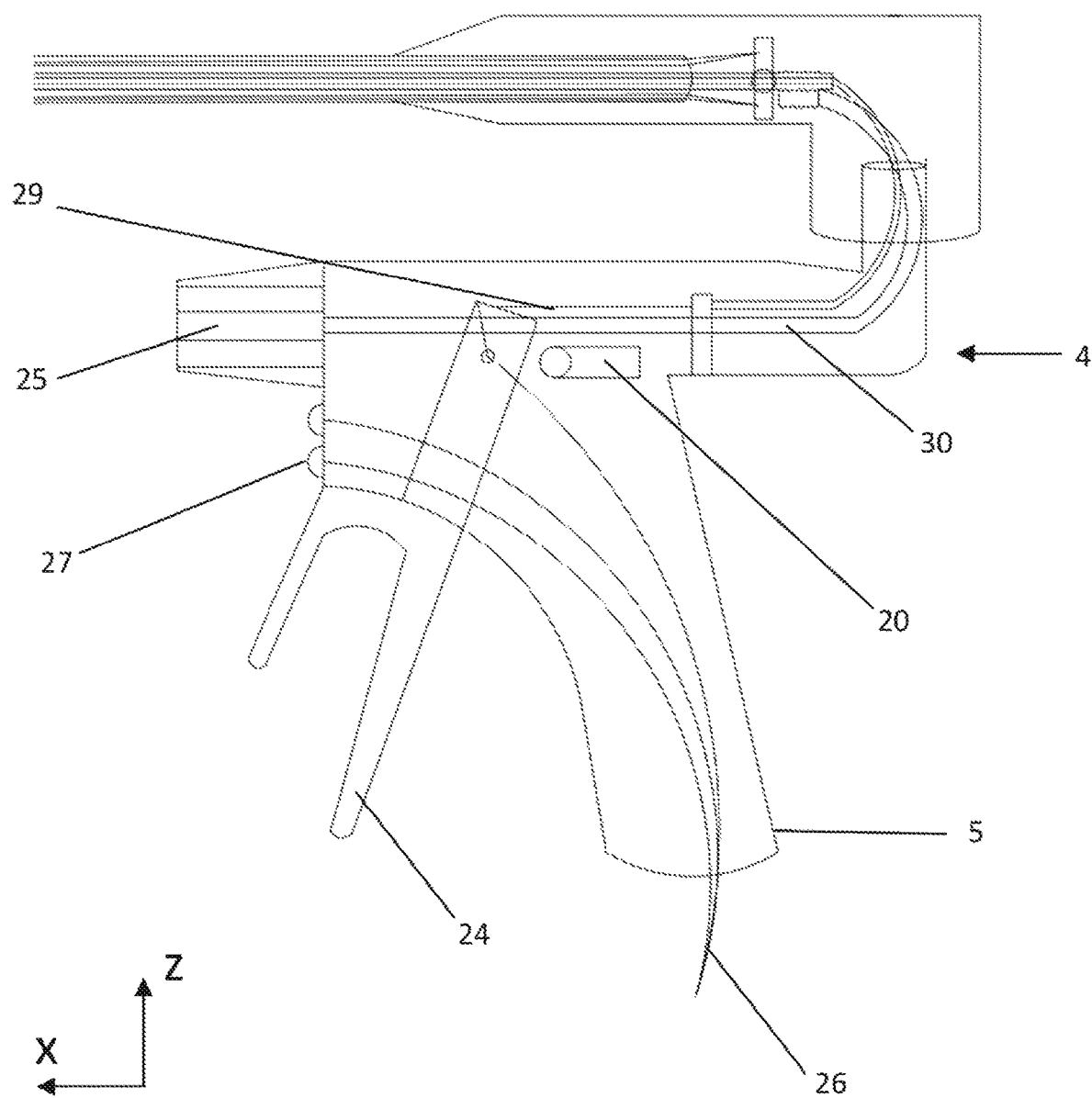
FIG. 10 is a schematic view showing the structure of a handle.

In another embodiment, an electrosurgical instrument is integrated to the blade part 1, the electrosurgical instrument can be a high-frequency electrotome, an ultrasonic knife or an argon gas knife. As shown in FIG. 10, the handle 4 is equipped with a power line 26 and an electrosurgical instrument switch 27, which are used to power and control the electrosurgical instrument.

The handle 4 is equipped with a blade switch rod 24 and a blade rotating knob 25. As shown in FIG. 10, blade controlling wire 29 passes through the shaft 2, one end of which is connected with the blade part 1 and the other end is connected with the blade switch rod 24. In operation, the blade switch rod 24 can be pulled to drive the blade controlling wire 29 to open or close the blade part 1. The blade rotating knob 25 connects with the blade part through an elastic shaft 30, and the blade rotating knob 25 can drive the blade part to rotate around the x axis. The blade switch rod 24 and the grip portion of the grip part 5 are arranged in a herringbone pattern, so that the user can hold the grip part 5 with the palm against the grip portion, and pull the blade switch rod 24 with fingers, to open or close the blade part 1. The blade rotating knob 25 is set in a upper location above the blade switch rod 24, so that the user can turn the blade rotating knob 25 with the index finger to make the blade part 1 to rotate around the x axis. The locking switch 20 is arranged on the side of the grip part 5, so that the user can turn the locking switch to lock blade joint assembly 2 with the thumb. The electrosurgical instrument switch 27 is arranged under the blade rotating knob 25, so that the user can operate the electrosurgical instrument with the index finger when holding the grip part 5. Depending on the kind of the electrosurgical instruments integrated by the knife head 1, the operations include high frequency electric cutting, electric coagulation, ultrasonic cutting, ultrasonic coagulation, argon plasma coagulation or other surgical actions.

As shown in FIG. 8, when the pivot 17 with the second axis rotates around the first axis 14 with the axle part 8 and is unparalleled to the y axis and the fourth axis 19 of the of the controlling wire joint assembly. In this case, the user holds the grip part 5 and rotates around the with the second axis 17. As shown in FIG. 9, the push-rod-plate 10 produces a motion component in the y-axis direction. Additional bending moments borne by the fulcrum rod 9 and the push rods 11 maintains the movement of the four-link mechanism consisting of the push-rod-plate 10, push rods 11 and the controlling wire joint assembly 12.

Figure 11:
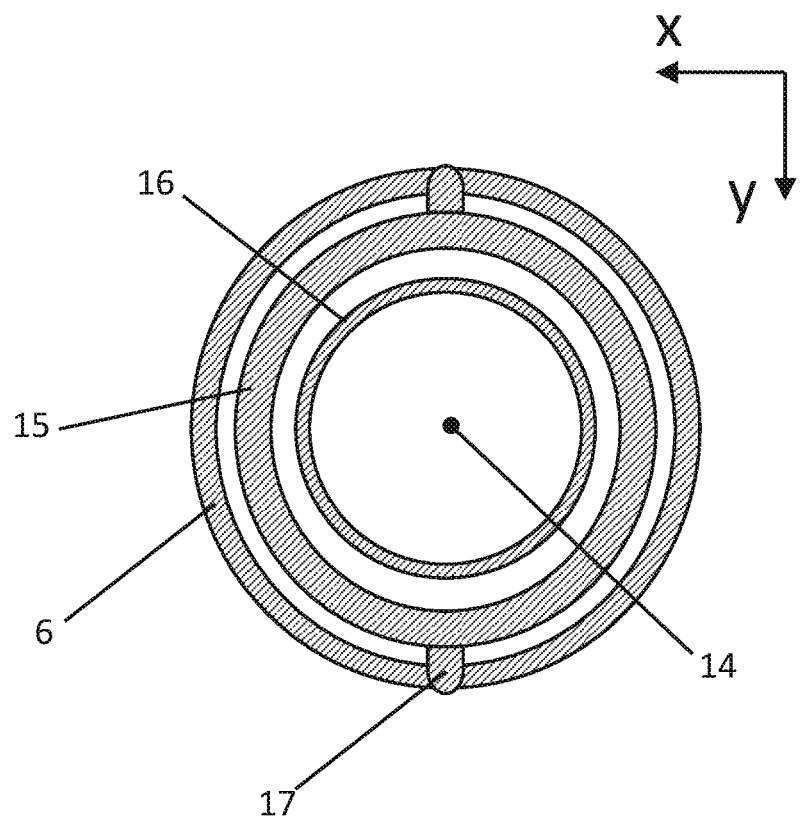
FIG. 11 is sectional view of a handle joint assembly.

This situation can be optimized by a preferable embodiment illustrated by FIG. 11: the inner cylinder 16 of the grip part joint assembly is directly installed on the axle part 8 and nested with the outer cylinder 15, and the axle part 8 can rotate around the first axis 14 relative to the outer cylinder 15. The outer cylinder 15 with the first axis is connected with the shell through the pivot 17 with the second axis, so that the axle part 8, the inner cylinder 16 and the outer cylinder 15 can rotate around the pivot 17 with the second axis.

When the grip part 5 rotates around the pivot 17 with the second axis, the outer cylinder is driven to rotate together; when the grip part 5 rotates around the first axis 14, the parallel relationship between the pivot 17 with the second axis and the y-axis is remained, thereby ensuring that the pivot 17 with the second axis is always paralleled with the fourth axis 19 of the controlling wire joint assembly. So that interference between the grip part 5 rotating around the first axis 14 and the grip part 5 rotating around the pivot 17 with the second axis is eliminated, reducing the additional stress on the controlling mechanism caused by the combined movements of grip part 5 simultaneously rotating around the first axis 14 and around the pivot 17 with the second axis, improving the service life of the parts and optimizing the smoothness of the bending movement of the blade joint assembly 2.

Figure 13:
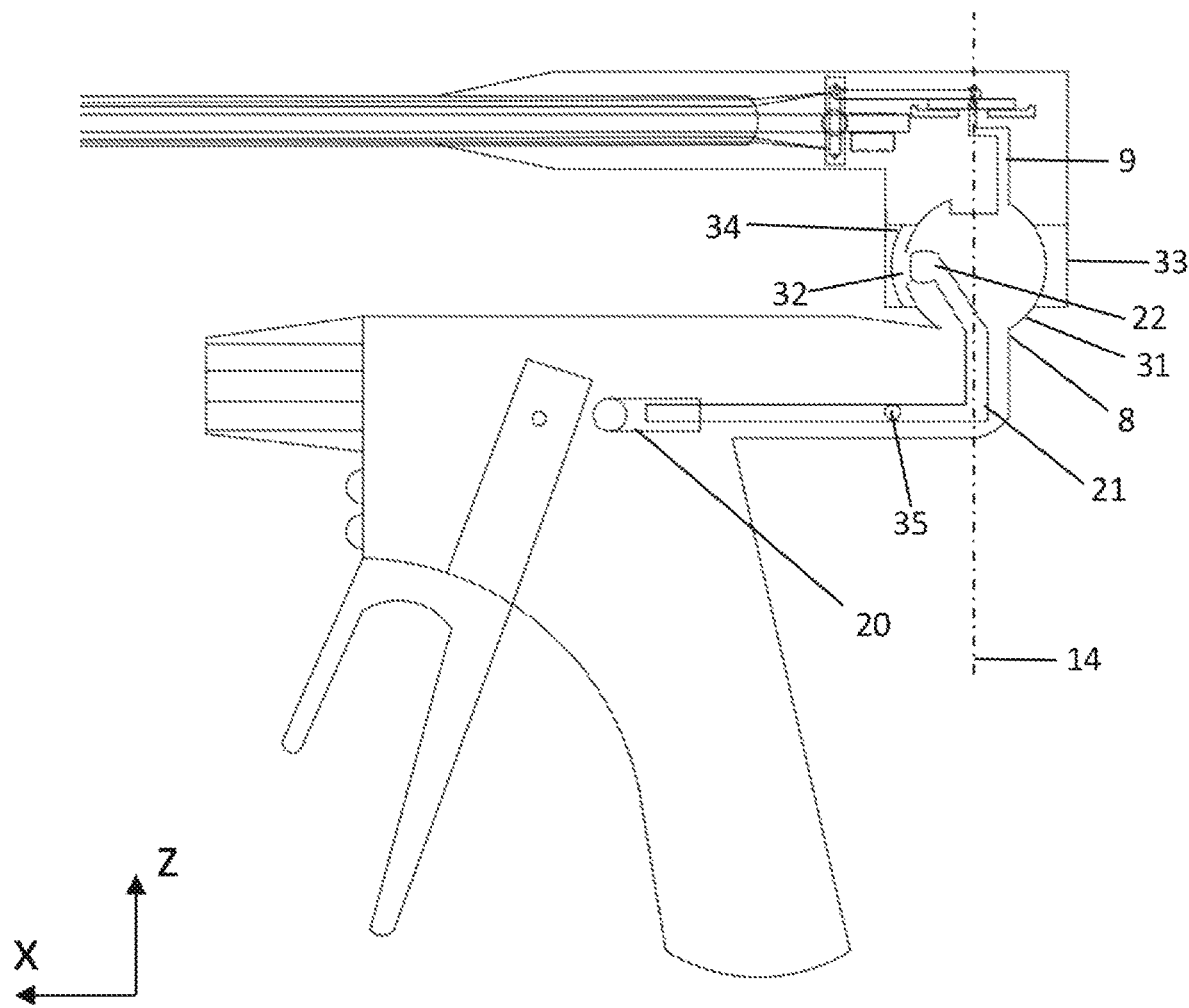
FIG. 13 is a schematic view showing the structure of a handle joint assembly.

In another embodiment, as shown in FIG. 13, the handle joint assembly is a ball joint, comprising the joint ball 31 and the support socket 33, the joint ball 31 is arranged on the top of the axle part 8, and the fulcrum rod 9 is connected with the joint ball 31. The axis of the opening of the support socket 33 is the first axis 14, and the axis parallels to the y axis of the joint ball is the second axis. Ball joint allows the grip part to rotate around the first axis 14 and swing in the xz-plane. A brake window 32 is arranged on the joint ball 31, and a rubber brake pad 34 is arranged on the inner side of the support socket 33 corresponding to the brake window 32. The locking switch 20 is connected with the brake 22 with a rubber pressing part through the locking transmission part 21. The locking transmission part 21 is a lever fixed on the brake pivot 35. When the locking switch 20 is turned, the handle, locking transmission 21, rotates around the brake pivot 35, driving the brake 22 pass through the brake window 32 and press the brake pad 34, so that the joint ball 31 is locked by the friction and cannot rotate relative to the support socket 33, and braking is achieved. The ball joint can reduce the parts of the handle joint assembly, simplifying manufacturing and maintenance.

Preferably, the support socket 33 is provided with a positioner, so that the joint ball can only rotate around the z axis and the y axis, but cannot rotate around the x axis, so as to reduce the additional moment borne by the fulcrum rod 9, and improve the reliability of the parts.

Preferably, the brake pivot 35 is provided with a spring shaft. When the locking switch 20 is turned to the releasing position, the elasticity of the spring shaft boosts the rotation of the lever 21, so that the brake 22 and the brake pad 34 can be rapidly separated, improving the agility of the brake termination process of mechanical arm, and optimizing the effectiveness of the operation.

In another embodiment, a rubber brake piece is arranged on the outside of the joint ball 31. One end of the locking transmission 21 is connected with the brake switch 20, and the other end is connected with a brake rod installed in the support socket 33. The brake rod is provided with a rubber pressing part that fits the arc surface of the joint ball. When the brake switch 20 is pulled, the locking transmission 21 drives the brake rod to press the brake piece from the outside of the joint ball 31. The joint ball 31 is prevent from rotating relative to the support socket 33 by the friction, achieving the braking. The pressing part of the brake rod is arranged on the outside of the joint ball 31, improving the contact area that contributes to the friction, and achieving braking more effectively.

Figure 14:
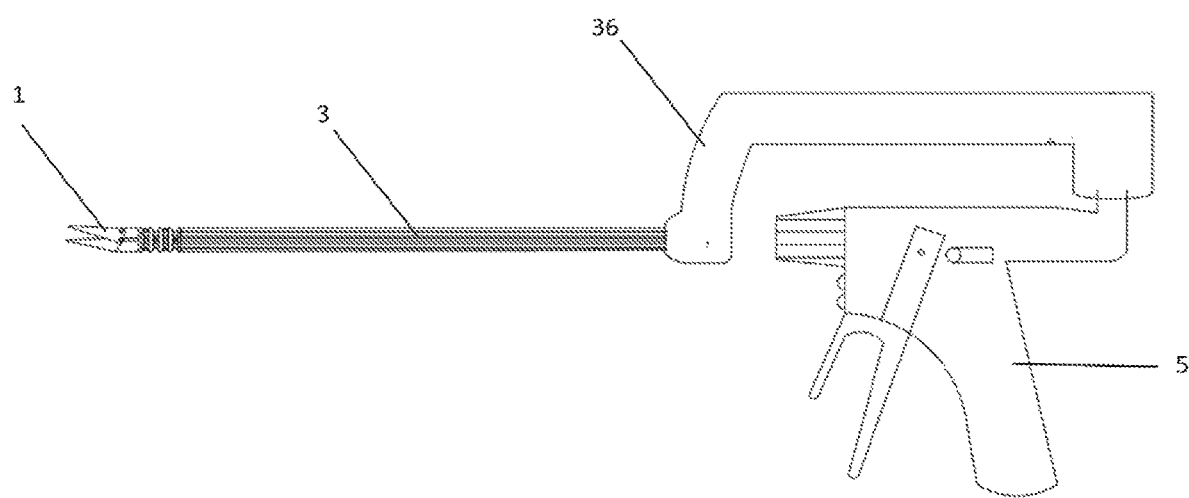
FIG. 14 is a schematic view showing the structure of a mechanical arm.

In another embodiment, as shown in FIG. 14, there is a bending segment 36 on the shaft 3, so that the blade part 1 and the upper end of the grip part 5 are in the same axis, thus the operation of the mechanical arm matches operation habits of laparoscopic instruments.

The purpose of the above embodiments is to provide a more detailed description of the disclosure in conjunction with the attached drawings so that the person in the art can achieve a better understanding of the technical concept of the disclosure, rather than to constitute a limitation on the embodiments of the disclosure. Within the scope of the claimed rights of the disclosure, equivalent replacement and improvement of the parts and structures of the disclosure, or combination of the embodiments without structural conflict, are all within the protection scope of the disclosure.

What is claimed is:

1. A portable minimally invasive surgical mechanical arm with multi-degree of freedom comprising a blade part, a blade joint assembly, a shaft and a handle;
   wherein the blade part is installed at one end of the shaft by the blade joint assembly, and the handle is installed at the other end of the shaft;
   the shaft comprises a plurality of controlling wires and a controlling wire joint assembly at the other end of the shaft;
   the controlling wire joint assembly and the blade joint assembly are connected by the plurality of controlling wires;
   wherein the handle comprises
      a grip part comprising a grip portion and an axle part, wherein the grip portion is used for holding;
      a handle joint assembly which is used to movably connect the axle part and comprises a first axis and a second axis that are mutually perpendicular to each other, and allows the axle part to rotate around the first axis and the second axis respectively, wherein the first axis coincides with an axis of the axle part and the second axis is perpendicular to the shaft; and
      a controlling mechanism connecting with the axle part and the controlling wire joint assembly, and used for transferring the movement of the grip part to the controlling wire joint assembly, and comprising a four-link mechanism;
   wherein the four-link mechanism comprises an input piece, two push rods and an output piece, and the two push rods are connected with the input piece and the output piece, the input piece is configured for receiving movements of the axle part and the output piece is a part of the controlling wire joint assembly.

2. The portable minimally invasive surgical mechanical arm with multi-degree of freedom claimed by claim 1, wherein the grip part is set on one side of the shaft, so that a holding direction of the grip part is intersected with an axial direction of the shaft.

3. The portable minimally invasive surgical mechanical arm with multi-degree of freedom claimed by claim 1, wherein the grip part comprises a shell fixedly installed with respect to the shaft,
   and the shell accommodates the handle joint assembly and the controlling mechanism;
   the handle joint assembly comprises an inner cylinder with the first axis as an axis,
   the inner cylinder is nested in the shell and can rotate around its own axis relative to the shell,
   the axle part is connected to the inner cylinder with a pivot and is axially aligned with the inner cylinder,
   and the pivot is arranged along the second axis.

4. The portable minimally invasive surgical mechanical arm with multi-degree of freedom claimed by claim 1, wherein the grip part comprises a shell fixedly installed with respect to the shaft,
   and the shell accommodates the handle joint assembly and the controlling mechanism;
   the handle joint assembly comprises an inner cylinder and an outer cylinder with the first axis as an axis,
   the axle part is set in the inner cylinder, and is rotatable around its own axis relative to the outer cylinder,
   the outer cylinder is connected to the shell with a pivot, and the pivot is arranged along the second axis.

5. The portable minimally invasive surgical mechanical arm with multi-degree of freedom claimed by claim 1, wherein the grip part comprises a shell fixedly installed with respect to the shaft,
   and the shell accommodates the handle joint assembly and the controlling mechanism;
   the handle joint assembly is a ball joint including a joint ball and a support socket,
   the joint ball is set at an end nearer to the shaft of the axle part,
   the support socket is fixed on the shell,
   and an axis of an opening of the support socket is the first axis.

6. The portable minimally invasive surgical mechanical arm with multi-degree of freedom claimed by claim 1, wherein the controlling wire joint assembly comprises a third axis and a fourth axis perpendicular to each other, allows the controlling wire joint assembly to rotate in the same direction with that the axle part rotating around the first axis and/or the second axis to drive the controlling wires, so that the blade joint assembly is driven to bend.

7. The portable minimally invasive surgical mechanical arm with multi-degree of freedom claimed by claim 1, wherein the input piece of the four-link mechanism is a push-rod-plate,
   and the center of the push-rod-plate is on the first axis,
   and the push-rod-plate is pivotedly connected with the axle part in the direction parallel to the second axis.

8. The portable minimally invasive surgical mechanical arm with multi-degree of freedom claimed by claim 1, wherein the handle comprises a locking system, the locking system comprises a locking switch, a locking transmission and a brake;

the locking switch is located on the grip part, and the locking switch is connected to one end of the locking transmission while the brake is connected to the other end of the locking transmission;

the locking switch has two states of locking and releasing, and when the locking switch is in the state of locking, the locking transmission drives the brake to a locking position to lock the handle joint assembly or the input piece of the four-link mechanism so that the four-link mechanism is frozen;

and when the locking switch is in the state of releasing, the brake moves out of the locking position leaving the input piece movable.

9. The portable minimally invasive surgical mechanical arm with multi-degree of freedom claimed by claim 8, wherein the handle comprises a blade switch rod and a blade controlling wire, the blade switch rod is connected with the blade part by the blade controlling wire for making the blade part open or close;

the blade switch rod is installed on the grip part, and the blade switch rod and the grip part are arranged in the shape of herringbone, so that a user can pull the blade switch rod with fingers when holding the grip portion in hand;

the handle comprises a blade rotating knob, the blade rotating knob is connected with the blade part by an elastic shaft for controlling the blade part rotating around its axis;

the blade rotating knob is installed on the grip part and is set in an upper location to the blade switch rod allowing a user to turn the blade rotating knob with ans index finger when holding the grip part;

the locking switch is located on one side of the grip part allowing a user to turn the locking switch with a thumb when holding the grip part.

10. The portable minimally invasive surgical mechanical arm with multi-degree of freedom claimed by claim 9, wherein the blade part comprises electrosurgical instruments, and both of the shaft and the handle contain power lines for the electrosurgical instruments;

the handle comprises an electrosurgical instrument switch which is adjacent to the blade rotating knob allowing a user to operate the electrosurgical instrument switch with an index finger when holding the grip portion.

11. The portable minimally invasive surgical mechanical arm with multi-degree of freedom claimed by claim 9, the axle part is hollow to allow the blade controlling wire and the elastic shaft extend through the axle part.

12. The portable minimally invasive surgical mechanical arm with multi-degree of freedom claimed by claim 1, wherein the shaft comprises a straight segment and a bending segment, and the straight segment and the handle are connected by the bending segment, and the grip part of the handle is located on an extension line of the straight segment.

* * * * *